United States Patent
Bae et al.

(10) Patent No.: US 11,077,125 B2
(45) Date of Patent: Aug. 3, 2021

(54) OPHTHALMIC COMPOSITION CONTAINING SULFASALAZINE AND HYALURONIC ACID

(71) Applicant: KUKJE PHARMA CO., LTD., Gyeonggi-do (KR)

(72) Inventors: Hyun Ju Bae, Gyeonggi-do (KR); Seung Ki Kim, Gyeonggi-do (KR); Beom Jung Kim, Gyeonggi-do (KR); Ju Hee Lee, Gyeonggi-do (KR); Young Gwan Kim, Gyeonggi-do (KR)

(73) Assignee: KUKJE PHARMA CO., LTD., Gyeonggi-Do (KR)

(*) Notice: Subject to any disclaimer, the term of this patent is extended or adjusted under 35 U.S.C. 154(b) by 0 days.

(21) Appl. No.: 16/469,969

(22) PCT Filed: Dec. 15, 2017

(86) PCT No.: PCT/KR2017/014798
§ 371 (c)(1),
(2) Date: Jun. 14, 2019

(87) PCT Pub. No.: WO2018/111021
PCT Pub. Date: Jun. 21, 2018

(65) Prior Publication Data
US 2020/0078375 A1    Mar. 12, 2020

(30) Foreign Application Priority Data
Dec. 16, 2016  (KR) .................... 10-2016-0172784

(51) Int. Cl.
*A61K 31/635*  (2006.01)
*A61K 9/00*  (2006.01)
*A61K 31/728*  (2006.01)
*A61K 47/34*  (2017.01)

(52) U.S. Cl.
CPC ......... *A61K 31/635* (2013.01); *A61K 9/0048* (2013.01); *A61K 31/728* (2013.01); *A61K 47/34* (2013.01)

(58) Field of Classification Search
CPC .. A61K 31/635; A61K 9/0048; A61K 31/728; A61K 47/34; A61K 2300/00
See application file for complete search history.

(56) References Cited

U.S. PATENT DOCUMENTS 8,524,280 B2    9/2013  Fatmi et al.

FOREIGN PATENT DOCUMENTS

| CN | 101987082 A | 3/2011 |
| KR | 10-2003-0023098 A | 3/2003 |
| KR | 10-2008-0092631 A | 10/2008 |
| KR | 10-2014-0054125 A | 5/2014 |
| KR | 10-1412776 B1 | 7/2014 |
| KR | 10-1587385 B1 | 1/2016 |
| KR | 10-1740869 B1 | 5/2017 |

OTHER PUBLICATIONS

International Search Report (ISR) from corresponding PCT Application No. PCT/KR2017/014798, dated Mar. 19, 2018, with English translation.

*Primary Examiner* — Barbara P Badio
(74) *Attorney, Agent, or Firm* — Harness, Dickey & Pierce, P.L.C.

(57) ABSTRACT

An ophthalmic composition containing sulfasalazine and hyaluronic acid is disclosed.

5 Claims, No Drawings

OPHTHALMIC COMPOSITION CONTAINING SULFASALAZINE AND HYALURONIC ACID

CROSS-REFERENCE TO RELATED APPLICATIONS

This application is a national phase application of PCT Application No. PCT/KR2017/014798, filed on Dec. 15, 2017, which claims the benefit and priority to Korean Patent Application No. 10-2016-0172784, filed on Dec. 16, 2016. The entire disclosures of the applications identified in this paragraph are incorporated herein by references.

FIELD

The present invention relates to an ophthalmic composition containing sulfasalazine or its salt and hyaluronic acid or its salt.

BACKGROUND

Sulfasalazine having a structure represented by the following formula 1 is a non-steroidal anti-inflammatory drug that is used for the treatment of colitis and enteritis, and is known to be also effective for the treatment of eye diseases such as retinal injury (see Korean Patent Application Laid-Open Publication No. 2003-0023098):

[Formula 1]

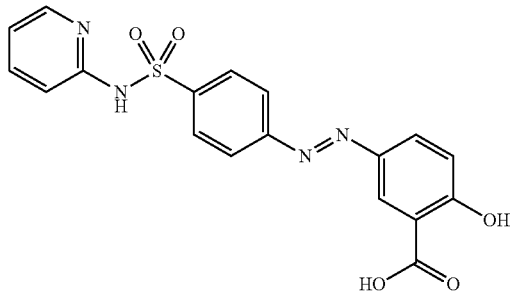

In addition, a mixture of sulfasalazine and hyaluronic acid (HA) is known to be effective for the treatment of eye diseases such as cataract and dry eye (see Korean Patent Application Laid-Open Publication No. 2008-0092631).

Sulfasalazine is practically insoluble in water (solubility: 0.0464 mg/ml). This solubility property of sulfasalazine is an obstacle to formulating sulfasalazine as a liquid ophthalmic composition for the treatment of eye diseases such as retinal injury.

Previously, a technology of forming a salt of sulfasalazine or PEGylating sulfasalazine to make sulfasalazine soluble in water was developed. However, this technology has a problem in that a salt-forming process or a PEGylation process needs to be added which makes the preparation process complicated and increases costs.

SUMMARY

Technical Problem

The present invention is intended to provide an ophthalmic composition containing sulfasalazine or its salt and hyaluronic acid or its salt, in which the ophthalmic composition improves the solubility and stability of the sulfasalazine. The ophthalmic composition according to the present invention may be used for the alleviation, prevention or treatment of dry eye and ophthalmologic diseases associated therewith.

Technical Solution

The present inventors have found that when a specific surfactant is used at a specific concentration, it may solubilize sulfasalazine and improve the stability of sulfasalazine.

Advantageous Effects

The composition of the present invention may improve the solubility and stability of sulfasalazine. Thus, the composition of the present invention may be useful for the alleviation, prevention or treatment of dry eye and ophthalmologic diseases associated therewith.

BEST MODE

The present invention is directed to an ophthalmic composition containing sulfasalazine or its salt and hyaluronic acid or its salt in an aqueous medium.

In the present invention, polyoxyethylene stearate (preferably, polyoxyl 40 stearate (Myrj S40 ™)) is used as a solubilizing agent to dissolve sulfasalazine in water.

Generally, polyoxyethylene stearate is generally recommended to be used in an amount of up to 7%.

However, the present inventors have found that when polyoxyethylene stearate is used in an amount of 2% or more, floating material occurs which reduces phase stability.

The present inventors have conducted studies, and as a result, found that when polyoxyethylene stearate is used in the composition according to the present invention in an amount of 0.01 to 2 wt %, preferably 0.2 to 1 wt %, most preferably 0.2 to 0.6 wt %, based on the total weight of the composition, a low-irritating composition, which has excellent phase stability without having to use an antioxidant (such as TPGS) or PVP and has significantly improved stability due to the long-term maintenance of the content of the active ingredient, may be prepared by using phosphate buffer or citrate buffer as a pH-adjusting agent in an aqueous medium.

Therefore, the present invention provides an ophthalmic composition containing sulfasalazine and hyaluronic acid, the ophthalmic composition further containing polyoxyethylene stearate and phosphate buffer or citrate buffer.

In addition, the composition according to the present invention may further contain, as a stabilizing agent, EDTA, beta-dextrin or its derivative, PVA (polyvinyl alcohol), alginic acid, PEG 400, hypromellose, etc.

The ophthalmic composition according to the present invention may be used for the treatment of eye diseases, such as retinal injury, cataract, conjunctivitis, or dry eye.

DETAILED DESCRIPTION

Examples

Hereinafter, the present invention will be described in detail with reference to examples in order to help understand the present invention. However, these examples are only illustrative of the present invention and may be modified into various different forms, and the scope of the present invention is not limited to these examples. These examples of the present invention are provided so that this disclosure will be thorough and complete, and will fully convey the scope of the present invention to those skilled in the art.

Example 1 Preparation of Compositions in Borax/Boric Acid Buffer

Using borax/boric acid buffer, the compositions shown in Table 1 below were prepared which contain Myrj S40, Cremophor EL or Tween 80 as a surfactant.

TABLE 1

Preparation of compositions in borax/boric acid buffer

| Purpose of addition | Components | Content (wt %) | | | | | | | | | | |
|---|---|---|---|---|---|---|---|---|---|---|---|---|
| | | Ex. 2-1 | Ex. 2-2 | Ex. 2-3 | Ex. 2-4 | Ex. 2-5 | Ex. 2-6 | Ex. 2-7 | Ex. 2-8 | Ex. 2-9 | Ex. 2-10 | Ex. 2-11 |
| Active ingredient | Sulfasalazine | 0.01 | 0.01 | 0.01 | 0.01 | 0.01 | 0.01 | 0.01 | 0.01 | 0.01 | 0.01 | 0.01 |
| | HA | 0.1 | 0.1 | 0.1 | 0.1 | 0.1 | 0.1 | 0.1 | 0.1 | 0.1 | 0.1 | 0.1 |
| Surfactant | Myrj S40 | 2 | 3 | 4 | 5 | — | — | — | — | — | — | — |
| | Cremophor EL | — | — | — | — | 2 | 3 | 4 | 5 | — | — | — |
| | Tween 80 | — | — | — | — | — | — | — | — | 2 | 3 | 4 |
| Buffer | Boric acid | 0.72 | 0.72 | 0.72 | 0.72 | 0.72 | 0.72 | 0.72 | 0.72 | 0.72 | 0.72 | 0.72 |
| | Borax | 0.323 | 0.323 | 0.323 | 0.323 | 0.323 | 0.323 | 0.323 | 0.323 | 0.323 | 0.323 | 0.323 |

Example 2 Preparation of Compositions in Citrate Buffer

Using citrate buffer, the compositions shown in Table 2 below were prepared which contain Myrj S40, Cremophor EL or Tween 80 as a surfactant.

TABLE 2

Preparation of compositions in citrate buffer

| Purpose of addition | Components | Content (wt %) | | | | | | | | | | |
|---|---|---|---|---|---|---|---|---|---|---|---|---|
| | | Ex. 3-1 | Ex. 3-2 | Ex. 3-3 | Ex. 3-4 | Ex. 3-5 | Ex. 3-6 | Ex. 3-7 | Ex. 3-8 | Ex. 3-9 | Ex. 3-10 | Ex. 3-11 |
| Active ingredient | Sulfasalazine | 0.01 | 0.01 | 0.01 | 0.01 | 0.01 | 0.01 | 0.01 | 0.01 | 0.01 | 0.01 | 0.01 |
| | HA | 0.1 | 0.1 | 0.1 | 0.1 | 0.1 | 0.1 | 0.1 | 0.1 | 0.1 | 0.1 | 0.1 |
| Surfactant | Myrj S40 | 2 | 3 | 4 | 5 | — | — | — | — | — | — | — |
| | Cremophor EL | — | — | — | — | 2 | 3 | 4 | 5 | — | — | — |
| | Tween 80 | — | — | — | — | — | — | — | — | 2 | 3 | 4 |
| Buffer | Citric acid | 0.0128 | 0.0128 | 0.0128 | 0.0128 | 0.0128 | 0.0128 | 0.0128 | 0.0128 | 0.0128 | 0.0128 | 0.0128 |
| | Sodium citrate | 0.45 | 0.45 | 0.45 | 0.45 | 0.45 | 0.45 | 0.45 | 0.45 | 0.45 | 0.45 | 0.45 |

Example 3 Preparation of Compositions in Trometamol Buffer

Using trometamol buffer, the compositions shown in Table 3 below were prepared which contain Myrj S40, Cremophor EL or Tween 80 as a surfactant.

TABLE 3

Preparation of compositions in citrate buffer

| Purpose of addition | Components | Content (wt %) | | | | | | | | | | |
|---|---|---|---|---|---|---|---|---|---|---|---|---|
| | | Ex. 4-1 | Ex. 4-2 | Ex. 4-3 | Ex. 4-4 | Ex. 4-5 | Ex. 4-6 | Ex. 4-7 | Ex. 4-8 | Ex. 4-9 | Ex. 4-10 | Ex. 4-11 |
| Active ingredient | Sulfasalazine | 0.01 | 0.01 | 0.01 | 0.01 | 0.01 | 0.01 | 0.01 | 0.01 | 0.01 | 0.01 | 0.01 |
| | HA | 0.1 | 0.1 | 0.1 | 0.1 | 0.1 | 0.1 | 0.1 | 0.1 | 0.1 | 0.1 | 0.1 |
| Surfactant | Myrj S40 | 2 | 3 | 4 | 5 | — | — | — | — | — | — | — |
| | Cremophor EL | — | — | — | — | 2 | 3 | 4 | 5 | — | — | — |
| | Tween 80 | — | — | — | — | — | — | — | — | 2 | 3 | 4 |
| Buffer | Trometamol | 0.121 | 0.121 | 0.121 | 0.121 | 0.121 | 0.121 | 0.121 | 0.121 | 0.121 | 0.121 | 0.121 |

Example 4 Preparation of Compositions in Phosphate Buffer

Using phosphate buffer, the compositions shown in Table 4 below were prepared which contain Myrj S40, Cremophor EL or Tween 80 as a surfactant.

TABLE 4

Preparation of compositions in phosphate buffer

| Purpose of addition | Components | Ex. 5-1 | Ex. 5-2 | Ex. 5-3 | Ex. 5-4 | Ex. 5-5 | Ex. 5-6 | Ex. 5-7 | Ex. 5-8 | Ex. 5-9 | Ex. 5-10 | Ex. 5-11 |
|---|---|---|---|---|---|---|---|---|---|---|---|---|
| Active ingredient | Sulfasalazine | 0.01 | 0.01 | 0.01 | 0.01 | 0.01 | 0.01 | 0.01 | 0.01 | 0.01 | 0.01 | 0.01 |
|  | HA | 0.1 | 0.1 | 0.1 | 0.1 | 0.1 | 0.1 | 0.1 | 0.1 | 0.1 | 0.1 | 0.1 |
| Surfactant | Myrj S40 | 2 | 3 | 4 | 5 | — | — | — | — | — | — | — |
|  | Cremophor EL | — | — | — | — | 2 | 3 | 4 | 5 | — | — | — |
|  | Tween 80 | — | — | — | — | — | — | — | — | 2 | 3 | 4 |
| Buffer | $Na_2HPO_4$ | 1.81 | 1.81 | 1.81 | 1.81 | 1.81 | 1.81 | 1.81 | 1.81 | 1.81 | 1.81 | 1.81 |
|  | $NaH_2PO_4$ | 0.56 | 0.56 | 0.56 | 0.56 | 0.56 | 0.56 | 0.56 | 0.56 | 0.56 | 0.56 | 0.56 |

Example 5 Test for Content Stability

For each of the compositions prepared in Examples 1 to 4, storage stability was tested by storing each composition under severe conditions (40° C., 100% relative humidity, shaking at 40 rpm, shaking water bath) for 2 weeks and then measuring the content of sulfasalazine. The results are shown in Tables 5 to 8 below.

TABLE 5

Results of measurement of the content of sulfasalazine in borax/boric acid compositions
Sulfasalazine content (%)

|  | Surfactant content | 2% | 3% | 4% | 5% |
|---|---|---|---|---|---|
| Myrj S40 | Initial[1] | 108.3 | 107.0 | 105.4 | 105.7 |
|  | After 2 weeks | 101.9 | 97.9 | 102.0 | 99.7 |
|  | Decrease (%) after 2 weeks | 6.4 | 9.1 | 3.4 | 6.0 |
| Tween80 | Initial | 109.8 | 102.7 | 101.1 | — |
|  | After 2 weeks | 85.2 | 84.7 | 81.0 | — |
|  | Decrease (%) after 2 weeks | 24.6 | 18.0 | 20.1 | — |
| Cremophor EL | Initial | 103.2 | 102.9 | 102.1 | 94.0 |
|  | After 2 weeks | 91.4 | 90.7 | 86.9 | 67.5 |
|  | Decrease (%) after 2 weeks | 11.8 | 12.2 | 15.2 | 26.5 |

1) According to Paragraph 1-1-C of Article 32 (establishment of specifications and standards of pharmaceuticals) of the Regulation on Pharmaceuticals Approval, Notification and Review (Ministry of Food and Drug Safety Notification No. 2016-120) in Republic of Korea, the active ingredient of a combination formulation may be contained in an amount of 90-110% based on the labeled amount. Thus, it can be understood that when the initial content is larger than 100%, the component was added in an amount above the labeled amount during composition preparation, and that when the initial content is smaller than 100%, the component was added in an amount below the labeled amount during composition preparation. This also applies to the following examples.

TABLE 6

Results of measurement of the content of sulfasalazine in citrate buffer compositions
Sulfasalazine content (%)

|  | Surfactant content | 2% | 3% | 4% | 5% |
|---|---|---|---|---|---|
| Myrj S40 | Initial | 108.6 | 108.6 | 103.7 | 100.6 |
|  | After 2 weeks | 108.6 | 108.4 | 103.7 | 100.6 |
|  | Decrease (%) after 2 weeks | 0.0 | 0.2 | 0.0 | 0.0 |
| Tween80 | Initial | 103.4 | 108.9 | 103.9 | — |
|  | After 2 weeks | 102.3 | 108.8 | 102.5 | — |
|  | Decrease (%) after 2 weeks | 1.1 | 0.1 | 1.4 | — |
| Cremophor EL | Initial | 104.2 | 114.7 | 108.3 | 118.8 |
|  | After 2 weeks | 103.4 | 114.3 | 108.1 | 116.9 |
|  | Decrease (%) after 2 weeks | 0.8 | 0.4 | 0.2 | 1.9 |

TABLE 7

Results of measurement of the content of sulfasalazine in trometamol buffer compositions
Sulfasalazine content (%)

|  | Surfactant content | 2% | 3% | 4% | 5% |
|---|---|---|---|---|---|
| Myrj S40 | Initial | 109.6 | 107.2 | 105.3 | 104.6 |
|  | After 2 weeks | 93.6 | 87.7 | 88.1 | 91.2 |
|  | Decrease (%) after 2 weeks | 16.0 | 19.5 | 17.2 | 13.4 |
| Tween80 | Initial | 110.5 | 107.9 | 108.9 | — |
|  | After 2 weeks | 81.8 | 89.8 | 74.6 | — |
|  | Decrease (%) after 2 weeks | 28.7 | 18.1 | 34.3 | — |
| Cremophor EL | Initial | 108.0 | 106.9 | 102.2 | 106.7 |
|  | After 2 weeks | 94.3 | 92.5 | 93.3 | 88.1 |
|  | Decrease (%) after 2 weeks | 13.7 | 14.4 | 8.9 | 18.6 |

TABLE 8

Results of measurement of the content of sulfasalazine in phosphate buffer compositions
Sulfasalazine content (%)

|  | Surfactant content | 2% | 3% | 4% | 5% |
|---|---|---|---|---|---|
| Myrj S40 | Initial | 106.2 | 105.5 | 108.8 | 104.4 |
|  | After 2 weeks | 103.0 | 105.3 | 105.3 | 103.5 |
|  | Decrease (%) after 2 weeks | 3.2 | 0.2 | 3.5 | 0.9 |
| Tween80 | Initial | 106.4 | 101.3 | 106.7 | — |
|  | After 2 weeks | 105.7 | 100.1 | 104.0 | — |
|  | Decrease (%) after 2 weeks | 0.7 | 1.2 | 2.7 | — |

TABLE 8-continued

Results of measurement of the content of sulfasalazine
in phosphate buffer compositions
Sulfasalazine content (%)

| | Surfactant content | 2% | 3% | 4% | 5% |
|---|---|---|---|---|---|
| Cremophor EL | Initial | 104.6 | 104.8 | 107.3 | 108.8 |
| | After 2 weeks | 102.5 | 102.9 | 104.7 | 105.9 |
| | Decrease (%) after 2 weeks | 2.1 | 1.9 | 2.6 | 2.9 |

From the test results, it was confirmed that in the borax/boric acid buffer and the trometamol buffer, the content stability of sulfasalazine was poor. In particular, in the trometamol buffer, a problem arose in that the pH of the compositions significantly changed.

However, in the citrate buffer and the phosphate buffer, the content stability of sulfasalazine was excellent. In addition, Myrj S40 showed excellent sulfasalazine content stability in all the four buffers tested.

Example 6 Preparation of Compositions Using Various Surfactants

Using citrate buffer and various surfactants, the compositions shown in Table 9 below were prepared.

TABLE 9

Preparation of various compositions in citrate buffer

| | | Amount (wt %) | | | | | | | |
|---|---|---|---|---|---|---|---|---|---|
| Purpose of addition | Components | Ex. 5-1 | Ex. 5-2 | Ex. 5-3 | Ex. 5-4 | Ex. 5-5 | Ex. 5-6 | Ex. 5-7 | Ex. 5-8 |
| Active ingredient | Sulfasalazine | 0.01 | 0.01 | 0.01 | 0.01 | 0.01 | 0.01 | 0.01 | 0.01 |
| | HA | 0.1 | 0.1 | 0.1 | 0.1 | 0.1 | 0.1 | 0.1 | 0.1 |
| Surfactant | RH40 | 2 | — | — | — | — | — | — | — |
| | HS15 | — | 2 | — | — | — | — | — | — |
| | Cremophor EL | — | — | 2 | — | — | — | — | — |
| | Myrj S40 | — | — | — | 2 | — | — | — | — |
| | Tyloxapol | — | — | — | — | 2 | — | — | — |
| | Tween 20 | — | — | — | — | — | 2 | — | — |
| | Tween 60 | — | — | — | — | — | — | 2 | — |
| | Tween 80 | — | — | — | — | — | — | — | 2 |
| Buffer | citric acid | 0.128 | 0.128 | 0.128 | 0.128 | 0.128 | 0.128 | 0.128 | 0.128 |
| | sod citrate | 0.45 | 0.45 | 0.45 | 0.45 | 0.45 | 0.45 | 0.45 | 0.45 |

Example 7 Test for Content Stability

For each of the compositions prepared in Example 6, storage stability was tested by storing each composition under accelerated conditions (40° C. and 75% relative humidity) for 4 months and then measuring the contents of sulfasalazine and HA. The results of the test are shown in Tables 10 and 11 below.

TABLE 10

Results of measurement of the content of sulfasalazine
in each composition of Example 6

| | | Content (%) | | Decrease (%) after |
|---|---|---|---|---|
| Sulfasalazine | Accelerated | Initial | 4 months | 4 months |
| | Tween20 | 102.9 | 102.1 | 0.8 |
| | Tween60 | 96.8 | 96.6 | 0.2 |
| | Tween80 | 104.1 | 69.4 | 34.7 |
| | ELP | 99.9 | 81.7 | 18.2 |
| | RH 40 | 98.1 | 96.3 | 1.8 |

TABLE 10-continued

Results of measurement of the content of sulfasalazine
in each composition of Example 6

| | | Content (%) | | Decrease (%) after |
|---|---|---|---|---|
| Sulfasalazine | Accelerated | Initial | 4 months | 4 months |
| | HS 15 | 102.3 | 101.3 | 1 |
| | Tyloxapol | 107.7 | 107.5 | 0.2 |
| | Myrj S40 | 99.5 | 98.9 | 0.6 |

TABLE 11

Results of measurement of the content
of HA in each composition of Example 6

| | | Content (%) | | Decrease (%) after |
|---|---|---|---|---|
| HA | Accelerated | Initial | 4 months | 4 months |
| | Tween20 | 95.3 | 90.5 | 4.8 |
| | Tween60 | 102.8 | 102.5 | 0.3 |
| | Tween80 | 98.2 | 94.4 | 3.8 |
| | RH 40 | 99.6 | 87.6 | 12 |
| | HS 15 | 97.6 | 88.6 | 9 |

TABLE 11-continued

Results of measurement of the content
of HA in each composition of Example 6

| | | Content (%) | | Decrease (%) after |
|---|---|---|---|---|
| HA | Accelerated | Initial | 4 months | 4 months |
| | Tyloxapol | 96.5 | 83.1 | 13.4 |
| | Myrj S40 | 95.1 | 93.2 | 1.9 |

From the test results, it could be seen that when Myrj S40 was used, the contents of sulfasalazine and HA and the pH of the composition were stably maintained.

The use of the remaining surfactants other than Myrj S40 showed a significant decrease in the content of sulfasalazine or HA. However, in the composition containing Myrj S40, the content stability of both sulfasalazine and HA was excellent.

Example 8 Measurement of pH Changes

Each of the compositions prepared in Example 6 was stored under accelerated conditions (40° C. and 75% relative humidity) for 4 months, and then the pH of each composition was measured to determine whether the pH would change. The results of the measurement are shown in Table 12 below.

TABLE 12

Results of measurement of pH changes in each composition of Example 6

| pH Accelerated | Initial | pH 4 months | Decrease after 4 months |
|---|---|---|---|
| Tween20 | 6.57 | 6.12 | 0.45 |
| Tween60 | 6.62 | 5.73 | 0.89 |
| Tween80 | 6.62 | 5.70 | 0.92 |
| ELP | 6.65 | 6.08 | 0.57 |
| RH 40 | 6.65 | 6.43 | 0.22 |
| HS 15 | 6.65 | 6.42 | 0.23 |

TABLE 12-continued

Results of measurement of pH changes in each composition of Example 6

| pH Accelerated | Initial | pH 4 months | Decrease after 4 months |
|---|---|---|---|
| Tyloxapol | 6.67 | 6.42 | 0.25 |
| Myrj52 | 6.42 | 6.42 | 0.00 |

From the measurement results, it was confirmed that when Myrj S40 was used, the pH was maintained at a constant level.

Thus, in the following examples, Myrj S40, which does not significantly decrease the contents of sulfasalazine and HA and maintains the pH at a constant level, was used as a surfactant.

Example 8 Preparation and Stability Test of Compositions Containing 4 wt % of Myrj S40

As shown in Table 13 below, compositions containing 4 wt % of Myrj S40 were prepared.

TABLE 13

Compositions containing 4 wt % of Myrj S40

| Purpose of addition | Components | pH 4 Ex. 8-1 | pH 5 Ex. 8-2 | pH 6 Ex. 8-3 | pH 7 Ex. 8-4 | pH 8 Ex. 8-5 |
|---|---|---|---|---|---|---|
| Active ingredient | Sulfasalazine | 0.01 | 0.01 | 0.01 | 0.01 | 0.01 |
| Active ingredient | HA | 0.1 | 0.1 | 0.1 | 0.1 | 0.1 |
| Surfactant | Myrj S40 | 4 | 4 | 4 | 4 | 4 |
| Buffer | Citric acid | 0.0128 | 0.0128 | 0.0128 | 0.0128 | 0.0128 |
| Buffer | Sodium citrate | 0.45 | 0.45 | 0.45 | 0.45 | 0.45 |

The results of measuring content stability and pH for the above compositions under severe conditions (40° C., 100% relative humidity, shaking at 40 rpm, and shaking water bath) are shown in Table 14 below.

TABLE 14

Results of content stability test

| Severe conditions | | Content (%) | | | | pH | | | | Remarks |
|---|---|---|---|---|---|---|---|---|---|---|
| | | Initial | 1 week | 1 month | 4 months | Initial | 1 week | 1 month | 4 month | |
| pH 4 | Sulfasalazine | 101.5 | 101.8 | 99.4 | 99.1 | 4.36 | 4.18 | 4.18 | 4.04 | |
| pH 5 | Sulfasalazine | 109.3 | 109.8 | 103.0 | 103.1 | 5.20 | 4.96 | 4.99 | 4.86 | |
| pH 6 | Sulfasalazine | 104.6 | 105.5 | 105.8 | 105.8 | 6.73 | 6.39 | 6.37 | 5.74 | Floating material occurred. |
| pH 7 | Sulfasalazine | 109.0 | 109.1 | 103.6 | 103.7 | 7.20 | 6.96 | 6.83 | 5.86 | Floating material occurred. |
| pH 8 | Sulfasalazine | 104.8 | 105.7 | 103.9 | 103.7 | 8.41 | 7.44 | 7.09 | 5.79 | Floating material occurred. |

From the test result, it could be seen that, at pH 6 or higher, floating material occurred in the compositions, thus reducing the phase stability of the compositions.

Example 13 Preparation of Compositions Containing 0.2 to 1.0 wt % of Myrj S40 and Containing Antioxidant and Stabilizing Agent As shown in Tables 15 to 18 below, compositions containing 0.2 to 1.0 wt % based on the total weight of each composition and also containing an antioxidant and a stabilizing agent were prepared.

TABLE 15

Compositions containing antioxidant and stabilizing agent

| Purpose of addition | Components | Amount (%) | | | |
|---|---|---|---|---|---|
| | | F-102 | F-103 | F-104 | F-105 |
| Active ingredient | Sulfasalazine | 0.01 | 0.01 | 0.01 | 0.01 |
| Active ingredient | HA | 0.1 | 0.1 | 0.1 | 0.1 |
| Surfactant | Myrj S40 | 0.2 | 0.4 | 0.6 | 1.0 |
| Stabilizing agent | EDTA | 0.01 | 0.01 | 0.01 | 0.01 |
| Antioxidant | TPGS[2] | 0.1 | 0.1 | 0.1 | 0.1 |
| Stabilizing agent | PVP K90 | 0.6 | 0.6 | 0.6 | 0.6 |
| Buffer | $Na_2HPO_4$ | 1.81 | 1.81 | 1.81 | 1.81 |
| Buffer | $NaH_2PO_4$ | 0.56 | 0.56 | 0.56 | 0.56 |

2) Tocopheryl (vitamin E) polyethylene glycol succinate.

TABLE 16

Compositions that do not contain both antioxidant and stabilizing agent PVP

| Purpose of addition | Components | Amount (%) | | | |
|---|---|---|---|---|---|
| | | F-107 | F-108 | F-109 | F-110 |
| Active ingredient | Sulfasalazine | 0.01 | 0.01 | 0.01 | 0.01 |
| Active ingredient | HA | 0.1 | 0.1 | 0.1 | 0.1 |
| Surfactant | Myrj S40 | 0.2 | 0.4 | 0.6 | 1.0 |
| Stabilizing agent | EDTA | 0.01 | 0.01 | 0.01 | 0.01 |
| Antioxidant | TPGS | — | — | — | — |
| Stabilizing agent | PVP K90 | — | — | — | — |
| Buffer | $Na_2HPO_4$ | 1.81 | 1.81 | 1.81 | 1.81 |
| Buffer | $NaH_2PO_4$ | 0.56 | 0.56 | 0.56 | 0.56 |

TABLE 17

Compositions containing no stabilizing agent PVP

| Purpose of addition | Components | Amount (%) | | | |
|---|---|---|---|---|---|
| | | F-112 | F-113 | F-114 | F-115 |
| Active ingredient | Sulfasalazine | 0.01 | 0.01 | 0.01 | 0.01 |
| Active ingredient | HA | 0.1 | 0.1 | 0.1 | 0.1 |
| Surfactant | Myrj S40 | 0.2 | 0.4 | 0.6 | 1.0 |
| Stabilizing agent | EDTA | 0.01 | 0.01 | 0.01 | 0.01 |
| Antioxidant | TPGS | 0.1 | 0.1 | 0.1 | 0.1 |
| Stabilizing agent | PVP K90 | — | — | — | — |
| Buffer | $Na_2HPO_4$ | 1.81 | 1.81 | 1.81 | 1.81 |
| Buffer | $NaH_2PO_4$ | 0.56 | 0.56 | 0.56 | 0.56 |

TABLE 18

Compositions containing no antioxidant

| Purpose of addition | Components | Amount (%) | | | |
|---|---|---|---|---|---|
| | | F-117 | F-118 | F-119 | F-120 |
| Active ingredient | Sulfasalazine | 0.01 | 0.01 | 0.01 | 0.01 |
| Active ingredient | HA | 0.1 | 0.1 | 0.1 | 0.1 |
| Surfactant | Myrj S40 | 0.2 | 0.4 | 0.6 | 1.0 |
| Stabilizing agent | EDTA | 0.01 | 0.01 | 0.01 | 0.01 |
| Antioxidant | TPGS | — | — | — | — |
| Stabilizing agent | PVP K90 | 0.6 | 0.6 | 0.6 | 0.6 |
| Buffer | $Na_2HPO_4$ | 1.81 | 1.81 | 1.81 | 1.81 |
| Buffer | $NaH_2PO_4$ | 0.56 | 0.56 | 0.56 | 0.56 |

Example 14 Results of Measurement of Content Stability and pH Stability for Compositions of Example 13

The results of measuring content stability and pH for the above compositions under accelerated conditions (40° C. and 75% relative humidity) are shown in Tables 19 to 21 below.

TABLE 19

Content of sulfasalazine

| Accelerated | Content (%) | | | | | | |
|---|---|---|---|---|---|---|---|
| | Initial | 1 month | 2 months | 3 months | 4 months | 5 months | 6 months |
| F-102 | 101.5 | 97.0 | 96.5 | 95.9 | 97.1 | 93.8 | 93.7 |
| F-103 | 107.1 | 97.2 | 96.6 | 96.8 | 97.4 | 95.9 | 95.0 |
| F-104 | 101.0 | 95.0 | 94.9 | 95.4 | 96.1 | 95.2 | 94.5 |
| F-105 | 107.1 | 95.6 | 93.0 | 89.8 | 91.6 | 90.2 | 90.1 |
| F-107 | 97.0 | 98.1 | 97.4 | 97.1 | 99.8 | 97.0 | 97.2 |
| F-108 | 95.7 | 97.5 | 97.0 | 96.1 | 96.4 | 94.3 | 94.0 |
| F-109 | 96.7 | 98.3 | 93.3 | 97.0 | 98.5 | 96.6 | 95.2 |
| F-110 | 97.0 | 97.5 | 97.7 | 95.7 | 96.3 | 94.9 | 95.4 |
| F-112 | 97.4 | 97.2 | 97.7 | 95.9 | 97.1 | 97.1 | 92.8 |
| F-113 | 98.7 | 98.1 | 98.3 | 97.6 | 98.5 | 96.3 | 96.6 |
| F-114 | 96.6 | 96.3 | 97.3 | 94.9 | 96.7 | 94.9 | 95.1 |
| F-115 | 95.6 | 95.6 | 91.7 | 94.8 | 95.1 | 92.0 | 89.0 |
| F-117 | 97.7 | 85.7 | Floating material occurred | Floating material occurred | Floating material occurred | Floating material occurred | Floating material occurred |
| F-118 | 96.8 | 75.5 | Floating material occurred | Floating material occurred | Floating material occurred | Floating material occurred | Floating material occurred |
| F-119 | 97.6 | 70.3 | Floating material occurred | Floating material occurred | Floating material occurred | Floating material occurred | Floating material occurred |

TABLE 19-continued

Content of sulfasalazine

| | Content (%) | | | | | | |
|---|---|---|---|---|---|---|---|
| Accelerated | Initial | 1 month | 2 months | 3 months | 4 months | 5 months | 6 months |
| F-120 | 95.5 | 75.6 | Floating material occurred | Floating material occurred | Floating material occurred | Floating material occurred | Floating material occurred |

TABLE 20

Content of HA

| | Content (%) | | | | | | |
|---|---|---|---|---|---|---|---|
| Accelerated | Initial | 1 month | 2 months | 3 months | 4 months | 5 months | 6 months |
| F-102 | 99.6 | 98.9 | 95.7 | 97.3 | 96.0 | 97.1 | 97.3 |
| F-103 | 100.7 | 100.2 | 99.4 | 99.0 | 99.6 | 99.5 | 99.2 |
| F-104 | 100.4 | 99.5 | 99.4 | 99.4 | 100.0 | 99.5 | 99.8 |
| F-105 | 101.1 | 101.3 | 97.2 | 96.4 | 95.0 | 95.2 | 94.8 |
| F-107 | 105.5 | 104.4 | 103.2 | 104.4 | 102.7 | 104.4 | 104.7 |
| F-108 | 98.8 | 98.3 | 98.1 | 98.4 | 97.5 | 97.1 | 98.4 |
| F-109 | 101.7 | 100.8 | 100.5 | 100.8 | 100.8 | 100.2 | 100.8 |
| F-110 | 108.8 | 106.0 | 103.2 | 104.6 | 105.4 | 104.7 | 105.0 |
| F-112 | 105.2 | 101.3 | 102.3 | 102.3 | 102.4 | 102.5 | 103.4 |
| F-113 | 109.4 | 101.2 | 108.4 | 108.4 | 99.9 | 106.8 | 105.4 |
| F-114 | 106.2 | 109.0 | 100.7 | 100.7 | 99.9 | 100.9 | 102.8 |
| F-115 | 104.8 | 103.1 | 104.1 | 107.9 | 100.5 | 102.0 | 101.9 |
| F-117 | 109.2 | 109.0 | Floating material occurred | Floating material occurred | Floating material occurred | Floating material occurred | Floating material occurred |
| F-118 | 108.7 | 107.6 | Floating material occurred | Floating material occurred | Floating material occurred | Floating material occurred | Floating material occurred |
| F-119 | 107.1 | 106.3 | Floating material occurred | Floating material occurred | Floating material occurred | Floating material occurred | Floating material occurred |
| F-120 | 106.1 | 105.0 | Floating material occurred | Floating material occurred | Floating material occurred | Floating material occurred | Floating material occurred |

TABLE 21 pH Changes

| | pH | | | | | | |
|---|---|---|---|---|---|---|---|
| Accelerated | Initial | 1 month | 2 months | 3 months | 4 months | 5 months | 6 months |
| F-102 | 7.19 | 7.16 | 7.19 | 7.12 | 7.13 | 7.09 | 7.22 |
| F-103 | 7.20 | 7.14 | 7.17 | 7.10 | 7.11 | 7.10 | 7.20 |
| F-104 | 7.21 | 7.17 | 7.18 | 7.09 | 7.12 | 7.11 | 7.19 |
| F-105 | 7.18 | 7.12 | 7.10 | 7.06 | 7.14 | 7.15 | 7.15 |
| F-107 | 7.12 | 7.13 | 7.06 | 7.10 | 7.12 | 7.10 | 7.25 |
| F-108 | 7.12 | 7.16 | 7.05 | 7.09 | 7.10 | 7.09 | 7.23 |
| F-109 | 7.15 | 7.13 | 7.03 | 7.12 | 7.12 | 7.12 | 7.20 |
| F-110 | 7.11 | 7.11 | 7.10 | 7.02 | 7.16 | 7.12 | 7.23 |
| F-112 | 7.17 | 7.17 | 7.08 | 7.15 | 7.10 | 7.10 | 7.22 |
| F-113 | 7.15 | 7.15 | 7.08 | 7.11 | 7.13 | 7.10 | 7.18 |
| F-114 | 7.15 | 7.17 | 7.07 | 7.14 | 7.12 | 7.15 | 7.17 |
| F-115 | 7.18 | 7.16 | 7.08 | 7.12 | 7.14 | 7.12 | 7.22 |
| F-117 | 7.13 | 7.14 | Floating material occurred | Floating material occurred | Floating material occurred | Floating material occurred | Floating material occurred |
| F-118 | 7.17 | 7.13 | Floating material occurred | Floating material occurred | Floating material occurred | Floating material occurred | Floating material occurred |

TABLE 21-continued pH Changes

| | | | pH | | | | |
|---|---|---|---|---|---|---|---|
| Accelerated | Initial | 1 month | 2 months | 3 months | 4 months | 5 months | 6 months |
| F-119 | 7.16 | 7.04 | Floating material occurred | Floating material occurred | Floating material occurred | Floating material occurred | Floating material occurred |
| F-120 | 7.15 | 7.16 | Floating material occurred | Floating material occurred | Floating material occurred | Floating material occurred | Floating material occurred |

From the test results, it was confirmed that when the stabilizing agent, such as PVP, or the antioxidant such as TPGS was used, a problem arose in that the content stability decreased or the floating material occurred. In addition, it was shown that when the surfactant was contained in an amount of 0.2 to 0.6 wt % based on the total weight of each composition, the content stability and the phase stability were excellent.

Example 15 Test for Measurement of Particle Size

The compositions shown in Table 22 below were prepared.

TABLE 22

Preparation of compositions

| Purpose of addition | Component | Amount (%) | | | | |
|---|---|---|---|---|---|---|
| | | F-121 | F-122 | F-123 | F-124 | F-125 |
| Active ingredient | Sulfasalazine | 0.01 | 0.01 | 0.01 | 0.01 | 0.01 |
| Active ingredient | HA | — | — | 0.1 | — | 0.1 |
| Surfactant | Myrj S40 | — | — | 0.2 | 0.2 | — |
| Stabilizing agent | EDTA | — | 0.01 | — | 0.01 | — |
| Buffer | Na$_2$HPO$_4$ | 1.81 | 1.81 | 1.81 | 1.81 | 1.81 |
| Buffer | NaH$_2$PO$_4$ | 0.56 | 0.56 | 0.56 | 0.56 | 0.56 |

For the above compositions, the particle size of sulfasalazine was measured using a Zeta potential particle size analyzer (ELSZ-1000, Otsuka Electronics) while storing each composition under severe conditions (40° C., 100% relative humidity, shaking at 40 rpm, and shaking water bath) for 1 week to 6 weeks. The results of the measurement are shown in Table 23 below.

TABLE 23

Results of particle size measurement

| | Size (nm) | | | | | |
|---|---|---|---|---|---|---|
| | Initial | 1 week | 2 weeks | 3 weeks | 4 weeks | 6 weeks |
| F-121 | 0.0 [3] | 0.0 | 0.0 | 0.0 | 1780.9 | 1854.9 |
| F-122 | 0.0 | 0.0 | 0.0 | 0.0 | 0.0 | 0.0 |
| F-123 | 54.7 | 90.6 | 210.8 | 245.3 | 334.7 | 854.4 |
| F-124 | 13.6 | 13.6 | 13.2 | 15.7 | 15.5 | 12.8 |
| F-125 | 206.0 | 191.6 | 749.8 | 2692.9 | 1051.1 | 2324.8 |

3) The fact that the particle size is "0" means that sulfasalazine was completely dissolved.

From the test results, it could be seen that when only sulfasalazine was dissolved, the particle size became larger after 4 to 6 weeks (see F-121). From the above test results, it can be seen that when Myrj S40 was used in the composition containing sulfasalazine and HA, the particle size of the sulfasalazine did not become larger. In particular, when the stabilizing agent EDTA was used, the particle size did not substantially increase.

Example 16 Test for Measurement of Particle Size

The compositions shown in Table 24 below were prepared.

TABLE 24

| Purpose of addition | Components | Amount (%) | | | |
|---|---|---|---|---|---|
| | | F-106 | F-107 | F-108 | F-109 |
| Active ingredient | Sulfasalazine | 0.01 | 0.01 | 0.01 | 0.01 |
| Active ingredient | HA | 0.1 | 0.1 | 0.1 | 0.1 |
| Surfactant | Myrj S40 | — | 0.2 | 0.4 | 0.6 |
| Stabilizing agent | EDTA | 0.01 | 0.01 | 0.01 | 0.01 |
| Buffer | Na$_2$HPO$_4$ | 1.81 | 1.81 | 1.81 | 1.81 |
| Buffer | NaH$_2$PO$_4$ | 0.56 | 0.56 | 0.56 | 0.56 |

For the above compositions, the particle size of sulfasalazine was measured using a Zeta potential particle size analyzer (ELSZ-1000, Otsuka Electronics) while storing each composition under severe conditions (40° C. and 75% relative humidity) for 3 months to 6 months. The results of the measurement are shown in Table 25 below.

TABLE 25

Results of particle size measurement

| | Size (nm) | | |
|---|---|---|---|
| | Initial | 3 months | 6 months |
| F-106 | 40.4 | 1097.1 | 1102.9 |
| F-107 | 14.6 | 14.9 | 14.2 |
| F-108 | 14.2 | 14.6 | 14.4 |
| F-109 | 14.6 | 14.4 | 14.5 |

From the test results, it can be seen that when only sulfasalazine was used as the active ingredient, EDTA alone could prevent the particle size from increasing (see F-112), but when both sulfasalazine and hyaluronic acid (HA) were used as the active ingredients, EDTA along could not prevent the particle size from increasing (see F-106). From the above results, it can be seen that when Myrj S40 is used, the particle size of sulfasalazine does not become larger. In particular, when Myrj S40 was used together with the stabilizing agent EDTA, the particle size did not substantially increase.

INDUSTRIAL APPLICABILITY

The ophthalmic composition according to the present invention improves the property stability, the content stability and the pH stability of sulfasalazine and HA.

What is claimed is:

1. An ophthalmic composition comprising, in an aqueous medium: sulfasalazine or its salt and hyaluronic acid or its salt as an active ingredient; and polyoxyl 40 stearate as a solubilizing agent,
    wherein the polyoxyl 40 stearate is contained in an amount of 0.01 to 2 wt % based on the total weight of the composition, and
    wherein the aqueous medium is phosphate buffer or citrate buffer.

2. The ophthalmic composition of claim 1, wherein the polyoxyl 40 stearate is contained in an amount of 0.2 to 0.6 wt % based on the total weight of the composition.

3. The ophthalmic composition of claim 1, wherein the composition further comprises a stabilizing agent.

4. The ophthalmic composition of claim 3, wherein the stabilizing agent is selected from the group consisting of EDTA, beta-dextrin or its derivative, PVA (polyvinyl alcohol), alginic acid, PEG400, and hypromellose.

5. The ophthalmic composition of claim 4, wherein the composition does not contain PVP and TPGS.

* * * * *